(12) United States Patent
Noren et al.

(10) Patent No.: US 8,798,765 B2
(45) Date of Patent: Aug. 5, 2014

(54) DETERMINATION OF CARDIAC RESYNCHRONIZATION THERAPY SETTINGS

(75) Inventors: Kjell Noren, Solna (SE); Anders Bjorling, Solna (SE); Tomas Svensson, Stockholm (SE); Sven-Erik Hedberg, Kungsangen (SE); Allen Keel, San Francisco, CA (US); Stuart Rosenberg, Castaic, CA (US); Kyungmoo Ryu, Palmdale, CA (US)

(73) Assignee: St. Jude Medical AB, Jarfalla (SE)

( * ) Notice: Subject to any disclaimer, the term of this patent is extended or adjusted under 35 U.S.C. 154(b) by 332 days.

(21) Appl. No.: 13/471,167

(22) Filed: May 14, 2012

(65) Prior Publication Data
US 2012/0310296 A1 Dec. 6, 2012

Related U.S. Application Data

(60) Provisional application No. 61/491,634, filed on May 31, 2011.

(30) Foreign Application Priority Data

Sep. 9, 2011 (EP) .................................. 11180696

(51) Int. Cl.
*A61N 1/365* (2006.01)
*A61N 1/372* (2006.01)
*A61N 1/368* (2006.01)

(52) U.S. Cl.
CPC ......... *A61N 1/36507* (2013.01); *A61N 1/37252* (2013.01); *A61N 1/3682* (2013.01); *A61N 1/3684* (2013.01)
USPC ...................... 607/62; 607/7; 607/27; 607/63

(58) Field of Classification Search
USPC ............................................ 607/7, 27, 62, 63
See application file for complete search history.

(56) References Cited

U.S. PATENT DOCUMENTS

| 5,331,966 | A | 7/1994 | Bennett et al. |
|---|---|---|---|
| 5,514,163 | A | 5/1996 | Markowitz et al. |
| 6,522,923 | B1 | 2/2003 | Turcott |
| 6,751,504 | B2 | 6/2004 | Fishler |
| 6,804,555 | B2 | 10/2004 | Warkentin |
| 6,853,861 | B1 | 2/2005 | Obel et al. |
| 7,203,542 | B2 | 4/2007 | Obel |
| 7,778,706 | B1 | 8/2010 | Min |
| 7,848,807 | B2 | 12/2010 | Wang |
| 2009/0299423 | A1* | 12/2009 | Min .................................. 607/9 |
| 2010/0268059 | A1 | 10/2010 | Ryu et al. |
| 2011/0172728 | A1* | 7/2011 | Wang ............................... 607/7 |

OTHER PUBLICATIONS

Extended EP Search Report—EP App No. 11180696, filed Sep. 9, 2011.

\* cited by examiner

*Primary Examiner* — Christopher D Koharski
*Assistant Examiner* — Natasha Patel

(57) ABSTRACT

CRT settings for an implantable medical device are determined by applying pacing pulses to heart chambers of a scheme of different combinations of interchamber delays. A respective width parameter value representing an R or P wave width is determined for each such delay combination based on an ECG representing signal and the width parameter values are employed to estimate a parametric model defining the width parameter as a function of interchamber delays. Candidate interchamber delays that minimize the width parameter are determined from the parametric model and employed to determine optimal CRT settings. The technique provides an efficient way of finding optimal CRT settings when multiple pacing sites are available in a heart chamber.

19 Claims, 5 Drawing Sheets

DETERMINATION OF CARDIAC RESYNCHRONIZATION THERAPY SETTINGS

CROSS REFERENCE TO RELATED APPLICATIONS

This application claims the benefit of U.S. Provisional Application Ser. No. 61/491,634, filed May 31, 2011, and European Patent Application No. 11180696.4, filed Sep. 9, 2011.

TECHNICAL FIELD

The present embodiments generally relate to cardiac resynchronization therapy settings, and in particular to determining such settings for a system with multiple available pacing sites.

BACKGROUND

The conventional approach in cardiac resynchronization therapy (CRT) involves pacing from an electrode provided close to the right ventricular (RV) apex, an electrode on a transvenous left ventricular (LV) lead, typically in the lateral or postero-lateral vein, and optionally an electrode in the right atrium (RA).

In such a case, the optimal interventricular (VV) delay between RV and LV pacing pulses and the optimal atrioventricular (AV) delay between atrial and ventricular pacing need to be determined. Several prior art solutions to such an optimization problem have been suggested. U.S. Pat. No. 5,514,163 optimizes an AV delay based on far field R wave sense (FFRS) duration. U.S. Pat. Nos. 6,751,504 and 6,804,555 use the width of the QRS in order to set optimal VV delays. In another document, U.S. Pat. No. 7,848,807, optimal AV and VV delays are determined based on the width of a P wave from a sensed far-field electrocardiogram.

Recent studies have suggested that biventricular pacing from two LV sites results in an improved clinical outcome in CRT patients, likely due to improved hemodynamic response from dual-LV pacing, in comparison with conventional biventricular pacing. However, the number of possibilities to select electrodes and to set delays between electrodes increase dramatically with increasing number of electrodes required for having multiple pacing sites within a ventricle.

For instance, assume a case with two independent LV pacing pulses and that there are ten possible stimulation vectors to choose from for each pulse. In such a case, there are two separate VV delays (or expressed differently one VV delay and one intraventricular delay) to be tested. Further assume, that the VV delay could be of one out of ten defined values and the intraventricular delay could be one out of 16 different values. The two ventricles can be paced in two different ways: RV first or LV first. This ends up with 10×10×10×16×2=32,000 different combinations. It is obvious that it is not possible in real applications to test each such combination in order to find the optimal VV and intraventricular delays. Efficient optimization procedures are thereby needed.

U.S. Pat. No. 6,522,923 is directed towards finding optimal AV and VV delays by testing a set of randomly selected AV and VV delays within a defined AV/VV space. The most optimal of the tested AV and VV combinations is found and a new set of randomly selected AV and VV delays are tested within a smaller AV/VV space centered at the most optimal AV/VV-combination. This procedure is repeated multiple times with ever smaller AV/VV spaces until a final optimal combination of AV and VV delays is found.

There is, however, still a need for efficient techniques to determine optimal VV delays for a system having multiple pacing sites.

SUMMARY

It is a general objective to provide an efficient determination of interchamber delays as cardiac resynchronization (CRT) settings. It is a particular objective to provide such an efficient determination when multiple pacing sites are available for a heart chamber. These and other objectives are met by embodiments disclosed herein.

An aspect of the embodiments relates to a system for determining CRT settings. The system comprises an electrode connector connectable to a first electrode configured to be arranged in or in connection with a first heart chamber and $N \geq 2$ electrodes configured to be arranged in or in connection with a second heart chamber. A pulse generator generates pacing pulses that are applied to the heart chambers using the first electrode and the N electrodes. The system comprises a pulse generator controller configured to control the pulse generator to generate pacing pulses of a defined scheme of interchamber delays. The scheme defines a respective maximum interchamber delay, a minimum interchamber delay and an intermediate interchamber delay for each electrode of the N electrodes with regard to the timing of applying a pacing pulse to the first electrode. A width processor determines a respective width parameter value for each electrode of the N electrodes. The width parameter value represents a width of a resulting R wave, if the first and second chambers are the ventricles, or of a resulting P wave, if the first and second chambers are the atria. The R or P wave widths are determined from an electrocardiogram representing signal recorded for the heart. A model processor of the system estimates an $n^{th}$ order parametric model based on the width parameter values from the width processor. The parametric model defines the width parameter as a function of a respective interchamber delay for each electrode of the N electrodes. The parametric model is a second or higher order model, i.e. $n \geq 2$. A delay processor processes the parametric model in order to determine a respective candidate interchamber delay for each electrode of the N electrodes. The respective candidate interchamber delays minimize the width parameter as determined from the parametric model. CRT settings are then determined based on these N candidate interchamber delays and are stored in a memory of the system.

Another aspect of the embodiments relates to a method for determining CRT settings. The method comprises applying pacing pulses to a first electrode arranged in or in connection with a first heart chamber and $N \geq 2$ electrodes arranged in or in connection with a second heart chamber. The pacing pulses are applied of a defined scheme of interchamber delays defining, for each electrode of the N electrodes, a maximum interchamber delay, a minimum interchamber delay and an intermediate interchamber delay with regard to the timing of applying a pacing pulse to the first electrode. A width parameter value is determined, for each combination of N interchamber delays of the defined scheme, and represents a width of a resulting R wave or of a resulting P wave. An $n^{th}$ order parametric model defining the width parameter as a function of a respective interchamber delay for each electrode of the N electrodes is estimated based on the determined width parameter values. The parametric model is employed to determine, for each electrode of the N electrodes, a candidate interchamber delay that minimizes the width parameter. CRT settings are then obtained based on the N candidate interchamber delays.

BRIEF DESCRIPTION OF THE DRAWINGS

The invention, together with further objects and advantages thereof, may best be understood by making reference to the following description taken together with the accompanying drawings, in which.

DETAILED DESCRIPTION

Throughout the drawings, the same reference numbers are used for similar or corresponding elements.

The present embodiments generally refer to cardiac resynchronization therapy (CRT) and in particular to the determination of CRT settings for implantable medical devices (IMDs), such as pacemakers, cardioverters and intracardiac defibrillators (ICDs). The embodiments in particular determine such CRT settings for situations where multiple pacing sites are available in a heart chamber.

Recently, studies have been conducted on human heart failure (HF) patients where it was demonstrated that CRT with multiple pacing sites in one heart chamber generally lead to improvements for the patient in terms of improved left ventricular (LV) ejection fraction and end-systolic volume indicating significantly more reverse remodeling as compared to conventional CRT. Furthermore, the responder rate for the patients was higher as compared to a control group receiving traditional CRT treatment.

Thus, there is a clinical desire to enable CRT with multiple pacing sites within a heart chamber, such as a ventricle or atrium. However, having multiple possible pacing sites implies that the procedure of selecting CRT settings in the form of pacing delays, such as interventricular (VV) and interatrial (AA) delays, will become much more complex and time consuming. For instance, having two LV pacing sites and one right ventricular (RV) pacing site and with interventricular delays in the range of −60 ms to +60 ms in 10 ms steps would take a total search time of about 28 minutes if each interventricular measurement takes 10 s. The total CRT settings search time will increase much more with one additional LV pacing site, making an exhaustive CRT setting search almost infeasible in practice. Long CRT settings search times with the accompanying processing in the IMD will drain a significant amount of battery power from the IMD and thereby shorten the total operating time of the IMD.

The embodiments provide a highly efficient technique that enables usage of multiple pacing sites in a heart chamber with CRT and can still determine suitable CRT settings for the IMD but without the long and complex CRT setting search of the prior art.

Figure 1:
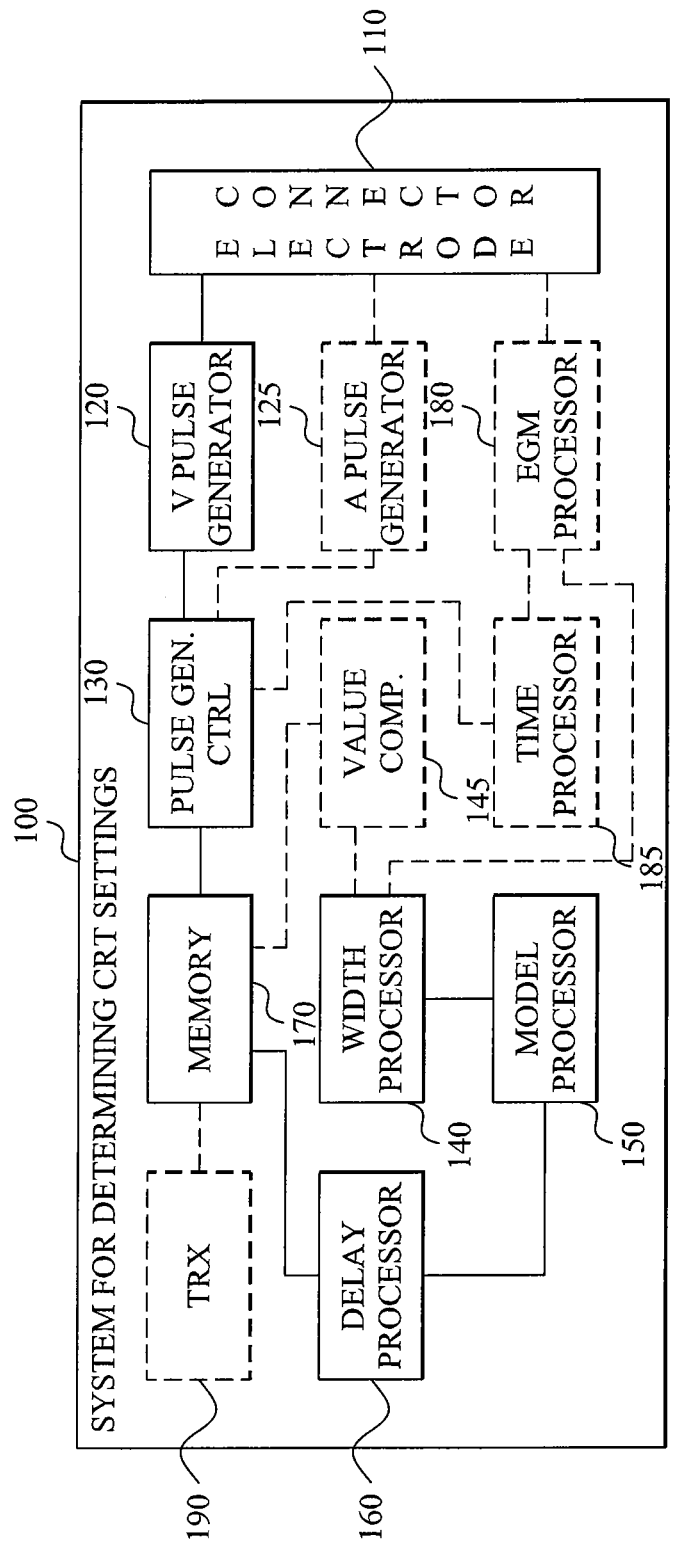
FIG. 1 is a schematic block diagram of a system for determining cardiac resynchronization therapy settings of an embodiment.

FIG. 1 is a schematic block diagram of a system 100 for determining CRT settings of an embodiment. The system 100 comprises an electrode connector 110 that is connectable to a first electrode configured to be arranged in or in connection with a first chamber of a subject's heart to thereby apply pacing pulses to the first heart chamber. The electrode connector 110 is also connectable to N electrodes configured to be arranged in or in connection with a second heart chamber. This number N is a positive integer equal to or larger than two. This means that multiple electrodes are available in or at the second heart chamber for delivery of pacing pulses to different sites of that heart chamber.

In a particular embodiment, the first electrode is provided on a first cardiac lead connectable to the electrode connector 110 and having the first electrode arranged in connection with its distal end and with its opposite proximal end connected to the electrode connector 110. Correspondingly, the N electrodes are advantageously arranged on a second cardiac lead connectable to the electrode connector 110. Alternatively, at least one of the N electrodes could be arranged on a second cardiac lead with the remaining electrode(s) of the N electrodes arranged on a third cardiac lead connectable to the electrode connector 110. In such a case, both the second and third cardiac leads are arranged in or in connection with the second heart chamber.

The first and second heart chambers are advantageously the right and left ventricles or the right and left atria. In such a case, the N electrodes are advantageously arranged in connection with the left ventricle or the left atrium but could, in other embodiments, instead be arranged in the right ventricle or the right atrium.

The system 100 illustrated in FIG. 1 also comprises a pulse generator 120, 125 connected to the electrode connector 110 and configured to generate pacing pulses that are applied by the first electrode and the N electrodes to the respective heart chambers. If the electrodes are provided in the right and left ventricles, the pulse generator is in the form of a ventricular pulse generator 120 and if the electrodes are provided in the right and left atria, the pulse generator is instead an atrial pulse generator 125. In some embodiments, electrodes are provided both in the atria and in the ventricles and then the system 100 could be provided with both a ventricular pulse generator 120 and an atrial pulse generator 125 as illustrated in FIG. 1. In an alternative embodiment, a single pulse generator is arranged in the system 100 for generating pacing pulses regardless of whether they are applied by electrodes to the atria or to the ventricles. There is then no need for a dedicated ventricular pulse generator 120 and a dedicated atrial pulse generator 125.

A pulse generator controller 130 is arranged in the system 100 connected to the pulse generator 120, 125 to control the pulse generator 120, 125 to generate pacing pulses of a defined scheme of interchamber delays. Of the embodiments, the defined scheme defines a maximum interchamber delay, a minimum interchamber delay and an intermediate interchamber delay for each electrode of the N electrodes. These interchamber delays of the defined scheme are with regard to the timing of applying a pacing pulse to the first electrode. Hence, the defined scheme defines three possible interchamber delays for each electrode and thereby each pacing site of the second heart chamber.

The system 100 further comprises a width processor 140 that is configured to process an electrocardiogram (ECG) representing signal recorded for the heart in order to determine respective width parameter values. Thus, for each combination of N interchamber delays of the defined scheme the width processor 140 determines a width parameter value representative of a width of a resulting specific wave characteristic in the ECG representing signal. This resulting specific wave characteristic is a resulting R wave if the first and second heart chambers are the right and left ventricles and is a resulting P wave if the first and second heart chambers are the right and left atria.

Measurements of the width of R and P waves can be done in several ways by the width processor 140. For example, the width parameter can be defined as the time the R or P wave is above a defined threshold. Another way to define the width parameter is the rise and fall time, i.e. the time the R or P wave is above a threshold set at, for instance, 10% of the wave amplitude. Yet another embodiment of a width parameter is the time from detection of electric activity in the first heart chamber to the peak of the R or P wave or the time difference between detection of electric activity in the first and second heart chambers. In the case of a width parameter value that is representative of the width of a resulting R wave, the width parameter value could represent the width of the QRS complex in the ECG representing signal. Generally, the R wave is the main feature of the QRS complex and using QRS width as a representation of R width is possible of the embodiments.

Thus, the embodiments are not limited to a particular technique of defining and measuring the width parameter value and can use any R or P width parameter known in the art, such as any of the ones mentioned above. However, once such a particular technique and parameter type have been selected it is consistently employed by the system 100 and the width processor 140 for the different combinations of N interchamber delays of the defined scheme.

The determined width parameter values from the width processor 140 are employed by a model processor 150 of the system 100 for estimating an $n^{th}$ order parametric model. This $n^{th}$ order parametric model defines the width parameter as a function of a respective interchamber delay for each electrode of the N electrodes.

The parameter n is a positive integer equal to or larger than two. This means that the parametric model is a second or higher order model. In a particular embodiment, the parametric model is a second order, i.e. quadratic, parametric model. Such a second order parametric model can efficiently be used to find suitable CRT settings in terms of interchamber delays that are at least close to the true optimal CRT settings. That is not possible with linear models since in such a case the optimal CRT settings found from a linear parametric model would always be found on the border, i.e. when at least one of the interchamber delays is set to its maximum interchamber delay value or its minimum interchamber delay value. Hence, second and higher order parametric models are needed in order to be able to find suitable CRT settings. Third, fourth and higher order parametric models are possible and can be used of the embodiments. However, in such a case more width parameter values and thereby more combinations of N interchamber delays need to be tested. Additionally, the computational power is higher when defining and using higher order parametric models as compared to a second order parametric model. In addition, higher orders parametric models have the risk of finding local optimal CRT settings, which makes it more difficult to find the global optimal CRT settings. In a particular embodiment, the parametric model is thereby a quadratic parametric model.

The quadratic parametric model estimated by the model processor 150 is advantageously defined as $$W_R = a + \sum_{i=1}^{N} b_i D_i + \sum_{i=1}^{N} c_i D_i^2 + \sum_{i=1}^{N-1} \sum_{j=i+1}^{N} e_{ij} D_i D_j,$$

wherein $W_R$ represents the width parameter and $D_i$, $D_j$ represents an interchamber delay for electrode i, j of the N electrodes. The model processor 150 thereby estimates the coefficients $a$, $b_i$, $c_i$, $e_{ij}$ of the quadratic parametric model based on the width parameter values obtained from the width processor 140 and based on information of the interchamber delays that are employed for the input width parameter values.

The system 100 also comprises a delay processor 160 that processes the $n^{th}$ order parametric model estimated by the model processor 150. In more detail, the delay processor 160 determines, based on the $n^{th}$ order parametric model and for each electrode of the N electrodes, the candidate interchamber delay that minimizes the width parameter. This means that the delay processor 160 uses the determined parametric model in order to find the candidate interchamber delay for each of the N electrodes that gives the smallest R or P width.

The candidate interchamber delays can be found by setting all partial derivatives to zero and solving the resulting equation systems with regard to the delays. It is also possible to use numerical methods, such as the Nelder-Mead algorithm, to find the candidate interchamber delays that minimize the width parameter from the parametric model.

The system 100 additionally comprises a memory 170 that stores CRT settings to be used by an IMD and where these CRT settings are obtained based on the N candidate interchamber delays determined by the delay processor 160.

In an embodiment, the CRT settings stored in the memory 170 are the N candidate interchamber delays as determined by the delay processor 160. The pulse generator controller 130 then controls the pulse generator 120, 125 to generate pacing pulses that are applied to the first electrode and the N electrodes based on the N candidate interchamber delays as CRT settings for the IMD.

In an embodiment, the N candidate interchamber delays determined by the delay processor 160 are stored directly in the memory 170 and used as CRT settings for the IMD as mentioned above. In an alternative approach, the N candidate interchamber delays are first tested and verified that they indeed result in the optimal R or P wave width. In such a case, the width processor 140 is configured to determine a candidate width parameter value occurring in the ECG representing signal recorded for the heart in response to the pulse generator controller 130 using the N candidate interchamber delays to control the pulse generator 120, 125. Thus, the pulse generator controller 130 controls the pulse generator 120, 125 to generate pacing pulses that are applied to the first electrode and the N electrodes based on the N candidate interchamber delays determined by the delay processor 160. This candidate width parameter value then represents the width of a resulting R or P wave obtained in the ECG representing signal when using the N candidate interchamber delays as CRT settings.

This embodiment of the system 100 preferably comprises a value comparator 145 configured to compare the candidate width parameter value with the width parameter values obtained in response to the pulse generator controller 130 controlling the pulse generator 120, 125 to generate pacing pulses applied to the first electrode and the N electrodes of the defined scheme. Thus, the value comparator 145 compares the candidate width parameter value with the width parameter values obtained during the processes of estimating the parametric model when the different combinations of N interchamber delays of the defined scheme are tested. These previously determined width parameter values are then stored by the width processor 140 in the memory 170 during the model estimating processes described in the foregoing.

If the candidate width parameter value is smaller than the previously determined width parameter values, the value comparator 145 generates a grant signal. This grant signal indicates that the memory 170 can store the N candidate interchamber delays as CRT settings. Thus, in this case, the N candidate interchamber delays determined by the delay processor 160 from the parametric model are the most optimal or suitable CRT settings as assessed by the minimization of the R or P wave width.

If the N candidate interchamber delays would not be the most suitable as determined when the candidate parameter width value is not smaller than all the stored width parameter values from the model estimation processes various actions can be taken. In an embodiment, the model estimation process can be repeated once more by testing the different combinations of N interchamber delays of the defined scheme or at least testing a portion thereof. New width parameter values are thereby available and can be used together with the previously determined width parameter values to determine a new n" order parametric model or an updated version of the present parametric model. The new or updated parametric model is then processed by the delay processor 160 to determine new candidate interchamber delays for the N electrodes. These new N candidate interchamber delays are then used by the pulse generator controller 130 to cause the pulse generator 120, 125 to apply pacing pulses to the first electrode and the N electrodes while an ECG representing signal is recorded for the subject. A new candidate width parameter value representing the width of the R or P wave in the ECG representing signal is determined by the width processor 140 and is tested by the value comparator 145 with the previously determined and stored parameter width values. If the new candidate width parameter value is the smallest, the new N candidate interchamber delays are stored in the memory 170 and employed as CRT settings. If they still would not be smallest a new test procedure testing at least a portion of the interchamber delays in the defined scheme can be started.

An alternative embodiment, which can be used in combination with the above described embodiment, is to allow the physician to inspect the N candidate interchamber delays before they are implemented as CRT settings. In such a case, the system 100 preferably comprises a transceiver (TRX) 190 or a transmitter and a receiver for enabling wireless, preferably RF-based, communication with a non-implantable data processing unit, such as a programmer or a physician's workstation equipped with a communication interface. The transceiver 190 transmits a notification of the iv candidate interchamber delays determined by the delay processor 160 to the data processing unit. There the physician can inspect them and modify them slightly if deemed, based on his/her medical experience and the particular subject, necessary and appropriate. The data processing unit then returns an implementation signal to the transceiver 190 of the system 100. In an embodiment, the implementation signal simply indicates to the system 100 that the determined N candidate interchamber delays can be stored and employed as CRT settings. In another embodiment, the implementation signal additional comprises any updated candidate interchamber delays as modified by the physician or information of the modification selected by the physician. In the former case, the system 100 stores and uses these updated candidate interchamber delays obtained based on the N candidate interchamber delays as CRT settings. In the latter case, the system 100 first updates the N candidate interchamber delays with the information in the implementation signal before storing and using them as CRT settings.

Figure 3:
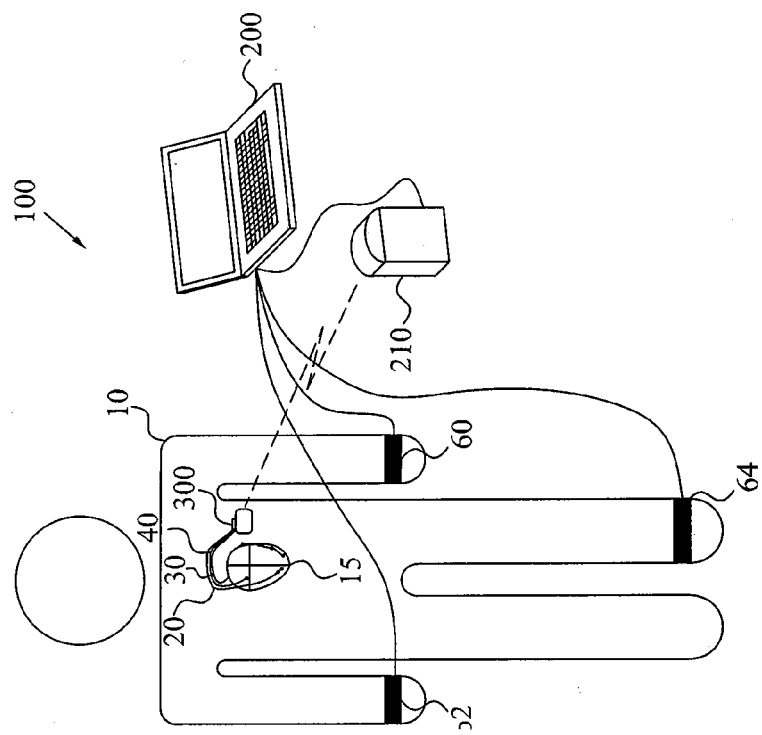
FIG. 3 is an illustration of a human subject and a system for determining cardiac resynchronization therapy settings of another embodiment.

The ECG representing signal employed by the width processor 140 in order to determine the width of the R or P waves for the different combinations of interchamber delays is advantageously a surface ECG or a surface-like ECG. FIG. 3 illustrates an embodiment where the subject 10 is connected to standard ECG cables with electrodes 60, 62, 64 placed on the skin surface of the subject 10 to record a surface ECG on the connected data processing unit 200, such as a programmer. The determination of the width parameter values can then be performed by the data processing unit 200 or the IMD 300 in the subject 10, which is further described herein.

Figure 2:
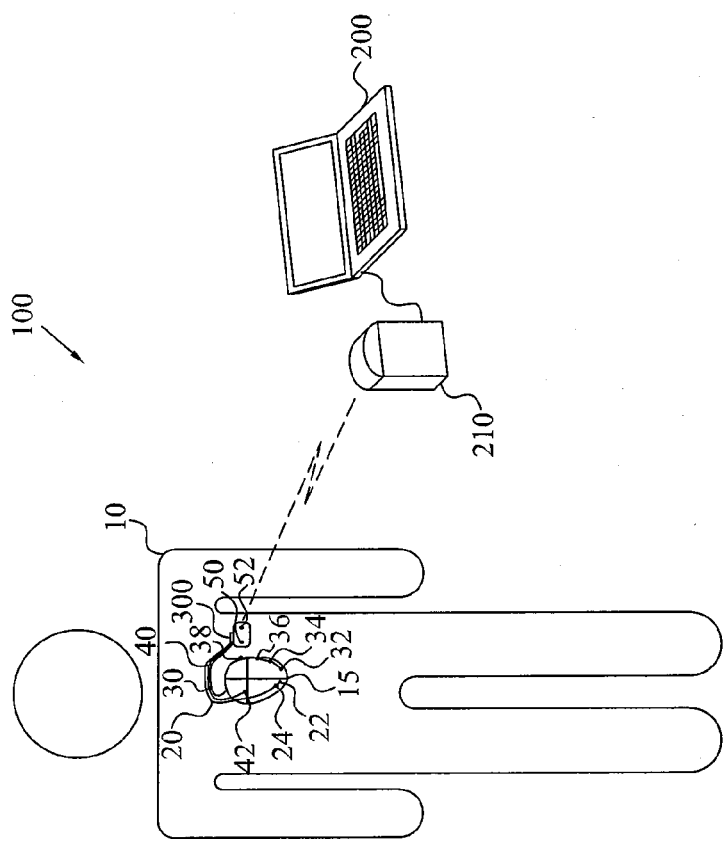
FIG. 2 is an illustration of a human subject and a system for determining cardiac resynchronization therapy settings of an embodiment.

If no surface ECG measurements are available implanted electrodes can be used to generate surface-like ECG signals. For instance, intracardiac electrogram (IEGM) signals can be recorded between implanted electrodes. In an embodiment, the IEGM signal is a global IEGM in terms of having a measurement vector selected to capture global cardiac events. For example, the IEGM signal can be measured between a superior vena cava (SVC) coil, RV coil, RA electrode or LV electrode and a case electrode on the IMD using an EGM processor 180 of the system 100. Another alternative is to have an IMD 300 with multiple case electrodes 50, 52 as indicated in FIG. 2. The IEGM signal recorded over these two case electrodes 50, 52 by the EGM processor 180 can then be used as surface-like ECG signal. A further alternative is to have a cardiac lead with a special sensing electrode close to the proximal end that is connectable to the electrode connector 110. The sensing electrode will then be positioned a distance from the heart and rather close to the device pocket in the subject. An IEGM signal that is recorded by the EGM processor 180 between the sensing electrode and a case electrode can be used as a surface-like ECG signal. Yet another solution is to have the electrode connector 110 connected to an extra lead that is placed in the device pocket in the subject or subcutaneously inferior to the IMD of the system 100. The extra lead then has a sensing electrode that can be used together with a case electrode to record an IEGM signal by the EGM processor 180 that can be used as surface-like ECG. Still a further alternative is to record multiple unipolar IEGM signals between different electrodes provided in or in connection with different heart chambers and the case electrode. The average of these multiple unipolar EGM signals will be a good representative of a surface-like ECG signal.

The defined scheme of interchamber delays used by the pulse generator controller 130 when controlling the pulse generator 120, 125 preferably comprises, for each electrode of the N electrodes, a maximum interchamber delay, a minimum interchamber delay and an intermediate interchamber delay equal to the average of the maximum and minimum delays for that electrode. Table 1 below illustrates an embodiment of such a defined scheme for a situation with N=3 and where the electrodes are ventricular electrodes and the interchamber delays are therefore interventricular delays.

TABLE 1 defined scheme of interventricular delays

| $V_R V_{L1}$ | $V_R V_{L2}$ | $V_R V_{L3}$ |
|---|---|---|
| Max | Max | Max |
| Max | Max | Min |
| Max | Min | Max |
| Max | Min | Min |
| Min | Max | Max |
| Min | Max | Min |
| Min | Min | Max |
| Min | Min | Min |
| Max | (Max + Min)/2 | (Max + Min)/2 |
| (Max + Min)/2 | (Max + Min)/2 | Max |
| (Max + Min)/2 | Max | (Max + Min)/2 |
| Min | (Max + Min)/2 | (Max + Min)/2 |
| (Max + Min)/2 | (Max + Min)/2 | Min |
| (Max + Min)/2 | Min | (Max + Min)/2 |
| (Max + Min)/2 | (Max + Min)/2 | (Max + Min)/2 |
| (Max + Min)/2 | (Max + Min)/2 | (Max + Min)/2 |
| (Max + Min)/2 | (Max + Min)/2 | (Max + Min)/2 |

Figure 5:
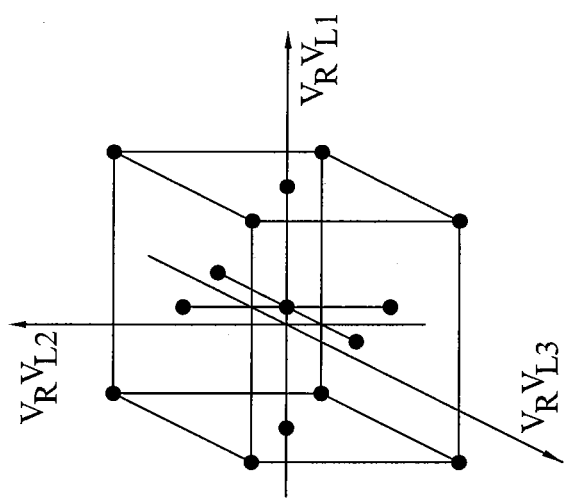
FIG. 5 schematically illustrates selection of interventricular delays of a defined scheme of interventricular delays of an embodiment.

The defined scheme is also visually illustrated in FIG. 5. In this embodiment, interchamber delays will be tested in a full factorial design. In Table 1 the three last rows have identical interchamber delays. This can be used in order to detect any variations within the data set that can occur due to naturally occurring variations between heart beats. Thus, although the defined scheme may test one or more combinations of interchamber delays several times, the defined scheme preferably only consists of the combinations of a full factorial design with a maximum interchamber delay, a minimum interchamber delay and one intermediate interchamber delay per electrode of the N electrodes.

In an alternative or additional approach to compensate for such naturally occurring variations each combination of interchamber delays is tested over multiple cardiac cycles. For instance, the pulse generator controller 130 can control the pulse generator 120, 125 to generate pacing pulses of each combination of N interchamber delays of the defined scheme during at least one respiratory cycle. The ECG representing signal could then be processed to determine an average ECG waveform over a cardiac cycle and the width parameter value is then determined for this average ECG waveform. An alternative is to determine one width parameter value for each cardiac cycle in the ECG signal for the particular combination of N interchamber delays and then calculate an average of these width parameter values.

The minimum and maximum values for the interchamber delays in the defined scheme could be the same for all interchamber delays. Alternatively, the maximum and/or minimum values for one interchamber delay can be different from the maximum and/or minimum values for another interchamber delay in the defined scheme.

The minimum and maximum values in the defined scheme can be predefined and stored in the memory 170 of the system 100. In such a case, basically the same minimum and maximum values and defined scheme are employed for all subjects for whom the system 100 determines CRT settings. In an alternative approach, the physician of the subject can set the maximum and minimum values to thereby get individually adjusted defined schemes. The system 100 then preferably receives a notification with its transceiver 190. The notification originates from the physician's data processing unit and defines the maximum interchamber delay and the minimum interchamber delay for each electrode of the N electrodes. This information of the maximum and minimum delays is entered in the memory 170, where they are available to the pulse generator controller 130.

The interchamber delays of the defined set could also be defined based on the paced interchamber conduction time if such a testing is performed by the system 100. The system 100 then preferably comprises a time processor 185 configured to determine a conduction time corresponding to a time from application of a pacing pulse at the first electrode and up to a time when a depolarization pulse is sensed at a given electrode of the N electrodes. The pulse generator controller 130 could then be configured to determine the maximum interchamber delay for the given electrode to be equal to the conduction time subtracted by a defined time value, such as 5-10 ms.

In a further embodiment, the system 100 has access to both a maximum interchamber delay value stored in the memory 170 or set by the physician and received from the transceiver, and information of the conduction time. In such a case, the pulse generator controller 130 could be configured to determine the maximum interchamber delay for the given electrode to be equal to the smallest of the conduction time subtracted by the defined time value and the maximum interchamber delay value stored in the memory 170 or set by the physician. This approach significantly prevents any intrinsic depolarization in the second ventricle, which otherwise could interfere with and thereby prolong the testing of the different interchamber delays of the defined scheme.

A further variant is that the system 100 transmits, using its transceiver 190, information of the conduction time and optionally the maximum interchamber delay value stored in the memory 170 to the physician's data processing unit. There the physician can decide which of the conduction time subtracted by the defined time value and the maximum interchamber delay value to use as the maximum interchamber delay for the given electrode. Information of the selected interchamber delay is then returned to the transceiver 190 and the system 100 and will be used by the pulse generator controller 130.

The values of the interchamber delays in the defined scheme are defined relative the timing of applying a pacing pulse to the first electrode. For instance, if the first electrode is a RV electrode and the N electrodes are different LV electrodes the defined scheme defines different values for the N interventricular delay. However, this is equivalent to define one interventricular delay and then N−1 intraventricular delays. Thus, instead of defining $V_R V_{L1}, V_R V_{L2}, \ldots, V_R V_{LN}$ the delays can be defined as $V_R V_{L1}, V_{L1} V_{L2}, \ldots, V_{L1} V_{LN}$. This is in fact equivalent since $V_{L1} V_{L2} = V_R V_{L1} - V_R V_{L2}$. Hence, a defined scheme of the embodiments setting values of interchamber delays also encompasses setting values of interchamber delay(s) and intrachamber delay(s).

The interchamber delays of the defined scheme can be positive, zero or even negative. A negative delay value implies that a pacing pulse is applied to the electrode of the N electrode prior application of a pacing pulse to the first electrode. For instance, an interchamber delay of −50 ms implies that the pacing pulse should be applied at the particular electrode at 50 ms before the application of a pacing pulse at the first electrode. Correspondingly, an interchamber delay of +60 ms implies that the pacing pulse is applied 60 ms after the application of the pacing pulse at the first electrode. This means that the first electrode can be paced first, last and theoretically also in the middle with regard to the N electrodes.

For some interchamber delay combinations, there may be spontaneous depolarization on one or more electrodes of the N electrodes. This effectively resembles no stimulation of this or these electrode(s). Determining which electrode(s) to stimulate will then implicitly be determined by the presence of inhibition.

The presence of inhibition by spontaneous depolarization during the evaluation phase when the system 100 determined the parametric model can be treated differently depending on IMD type and subject's disease. For instance, in case of a left bundle branch block (LBBB) HF subject it may be assumed a priori that the subject should have 100% LV pacing. In case inhibition occurs in this subject, the maximum value of the interventricular delays should be modified, typically reduced, to not create inhibition.

As an example, if the delay set $(V_R V_{L1}, V_R V_{L2}, V_R V_{L3})$= (Min, Max, Max)=(−80 ms, 80 ms, 80 ms) cause spontaneous depolarization on the electrodes LV2 and LV3 after 60 ms and 100 ms counting from the LV1 stimulation pulse, the maximum $V_R V_{L2}$ delay should be set to the minimum of Max and $V_R V_{L1}$+60 ms and the maximum $V_R V_{L3}$ delay to the minimum of Max and $V_R V_{L1}$+100 ms.

For other subjects, where stimulation on all LV electrodes is not an a priori requirement, the setting is typically kept and the pacing pulse simply inhibited.

The system 100 can be used, as previously mentioned, to determine CRT settings in terms of optimal interventricular delays, interatrial delays or both interventricular delays and interatrial delays. In the latter case, the system 100 can first generate an atrial parametric model and determine optimal interatrial delays and then determine a ventricular parametric model and determine optimal interventricular delays. The opposite order is also possible. Furthermore, since changing the interatrial delays will only affect the P wave width and changing the interventricular delays will only affect the R wave width, the interatrial and interventricular delay optimization can be made in any order, or even in parallel.

Generally, the width of the R wave can be influenced by the intrinsic atrioventricular (AV) conduction. This can be handled by setting the AV delay employed by the pulse generator controller 130 to a very small value during the optimization process when determining interventricular delays to thereby avoid intrinsic AV conduction. In such a case, fusion beats will not occur or at least occur very seldom as ventricular pacing occurs before intrinsic AV conduction. In such a case, the pulse generator controller 130 controls an atrial pulse generator 125 of the system 100 to generate pacing pulses to be applied to an atrial electrode connected to the electrode connector 110 and controls the ventricular pulse generator 120 to generate pacing pulses to be applied to the first ventricular electrode and the N ventricular electrodes of the defined scheme after expiry of a defined AV delay with regard to the timing of applying a pacing pulse to the atrial electrode. This defined AV delay is then set to be smaller than an average intrinsic AV conduction time of the heart.

Another way is to use whatever AV delay that has been programmed into the system 100. This AV delay may then lead to intrinsic AV conduction but that poses no limitations on the determination of the parametric model and the candidate interventricular delays. In this approach, it is preferred that suitable AV delays are first determined of well known techniques or set by the physician before the optimization of interventricular delays.

The system 100 can be configured to determine CRT settings in connection with implantation of an IMD of the system 100 in a subject. In such a case, the subject can be connected to surface ECG electrodes connected to a programmer that can communicate with the IMD of the system 100. The system 100 can alternatively or in addition operate for determining the CRT settings at one or more occasions after implantation. In such a case, the system 100 could be responsive to a trigger signal received by the transceiver 190 and originating from a non-implantable data processing unit, typically the physician's workstation or programmer. The trigger signal then triggers the pulse generator controller 130 to control the pulse generator 120, 125 to start pacing of the defined scheme of interchamber delays. This trigger signal can then also include information of the minimum and maximum interchamber delays to use for the defined scheme.

In an alternative approach, the system 100 itself triggers determination of CRT settings. Such a trigger could be the elapse of a defined timer. This approach implies that the system 100 periodically updates its CRT settings. The value of the defined timer can optionally be set by the physician and determined based on the particular heart condition and the particular subject. Example of suitable periods for updating the CRT settings could be once per week, once per month, one or a few times per year or even more seldom.

A further alternative is to determine CRT settings as described in the foregoing in connection with implantation of an IMD or upon reception of a trigger signal. Then the system 100 could update the CRT settings, optionally without any feedback or trigger signal from the physician. In such a case, the width processor 140 is configured to determine a candidate width parameter value representative of a width of a resulting wave in an ECG representing signal in response to the pulse generator controller 130 controlling the pulse generator 120, 125 to generate pacing pulses to be applied to the first electrode and the N electrodes based on the N candidate interchamber delays, unless such a candidate width parameter value already has been determined and stored in the memory 170. Thus, this candidate width parameter value is obtained when using the N interchamber delays determined by the delay processor 160, optionally modified slightly by the physician as previous mentioned.

The pulse generator controller 130 also controls the pulse generator 120, 125 to generate pacing pulses to be applied to the first electrode and the N electrodes based on a candidate interchamber delay of the N candidate interchamber delays modified with a delta delay. Thus, one of the candidate interchamber delays is modified slightly with a delta delay that could either be positive or negative. The value of this delta delay can be set by the physician and notified to the system 100 by a control signal received by the transceiver 190. In an alternative approach, the delta delay has a magnitude that is a fixed percentage, such as 1-5%, of the magnitude of the candidate interchamber delay to be tested.

The width processor 140 then determines an updated width parameter value representative of the width of a resulting R or P wave in the ECG representing signal recorded for the heart. This updated width parameter value thus reflects the updated R or P wave width obtained when using the N candidate interchamber delays with at least one of the interchamber delays modified with the delta delay.

The N interchamber delays stored as CRT settings in the memory 170 are then updated with the modified candidate interchamber delay if the updated width parameter value is smaller than the candidate width parameter value.

If the updated width parameter value instead would be larger than the candidate width parameter value the same interchamber delay can be tested anew but modified with the delta delay but with the opposite sign, i.e. negative value if the previous modification was with a positive value and vice versa. If instead the updated width parameter value is indeed smaller than the candidate width parameter value, the procedure can be repeated by adding a new delta delay to the particular interchamber delay and test whether this modified interchamber delay leads to even smaller R or P wave widths. This procedure can then be repeated with all interchamber delays or several such interchamber delays can be modified and tested together.

Another way to vary the interchamber delays is to test N+1 interchamber delay combinations, such as obtained by modifying different candidate interchamber delays with delta delays, and evaluate the result to see which interchamber delay combination that resulted in the worst result in terms of largest R or P wave width. This combination is then discarded and replaced by a new combination of interchamber delays that is perpendicular to the hyperplane spanned by the other combinations of interchamber delays. Out of these new delay combinations, the worst performing combination is again replaced by a new delay combination and the process is repeated. This type of optimization is called Nedler-Mead optimization.

In an embodiment, the system 100 is configured to determine interventricular delays as CRT settings. With reference to FIGS. 1-3, the electrode connector 110 is then connectable to a first ventricular lead 20 comprising the first ventricular electrode 22 and configured to be arranged in a first ventricle of the heart 15, the right ventricle in FIGS. 2 and 3. A second ventricular lead 30 comprising N ventricular electrodes 32, 34, 36 is configured to be arranged in or in connection with a second ventricle, the left ventricle in this example. The pulse generator is then a ventricular pulse generator 120 and the pulse generator controller 130 controls the ventricular pulse generator 120 to generate pacing pulses to be applied to the first ventricular electrode 22 and the N ventricular electrodes 32, 34, 36 of a defined scheme of interventricular delays. The width processor 140 determines an R width parameter value for each combination of N interventricular delays of the defined scheme based on the ECG representing signal recorded for the heart. The model processor 150 estimates a parametric model based on the R width parameter values and where this parametric model defines the R width parameter as a function of a respective interventricular delay for each ventricular electrode of the N ventricular electrodes 32, 34, 36. The parametric model is processed by the delay processor 160 in order to determine the N candidate interventricular delays that minimize the R width parameter. These determined N candidate interventricular delays are stored as CRT settings or employed to determine CRT settings, which are entered in the memory 170.

In another embodiment, the system 100 is configured to determine interatrial delays as CRT settings. The electrode connector 110 is then connectable to a first atrial lead 40 comprising the first atrial electrode 42 and configured to be arranged in a first atrium of the heart. A lead comprising N atrial electrodes is configured to be arranged in or in connection with a second atrium. The pulse generator is then an atrial pulse generator 125 and the pulse generator controller 130 controls the atrial pulse generator 125 to generate pacing pulses to be applied to the first atrial electrode 42 and the N atrial electrodes of a defined scheme of interatrial delays. The width processor 140 then determines a P width parameter value for each combination of N interatrial delays of the defined scheme based on the ECG representing signal recorded for the heart. The model processor 150 estimates a parametric model based on the P width parameter values and where this parametric model defines the P width parameter as a function of a respective interatrial delay for each atrial electrode of the N atrial electrodes. The parametric model is processed by the delay processor 160 in order to determine the N candidate interatrial delays that minimize the P width parameter. These determined N candidate interatrial delays are stored as CRT settings or employed to determine CRT settings, which are entered in the memory 170.

In a further embodiment, the system 100 determines both optimal interventricular delays as described above and interatrial delays. In a particular embodiment, a first atrial electrode 42 is configured to be arranged in or in connection with a first atrium of the heart, whereas M atrial electrodes 38 are arranged in or in connection with a second atrium of the heart, where M is a positive integer equal to or larger than one. The operation of the system 100 with regard to determining interatrial delays is basically the same as disclosed above.

This approach is possible with a so-called multipolar lead, such as a quadropolar lead 30 that is implanted in connection with the left ventricle. A left ventricular lead 30 is typically implanted in the coronary venous system, e.g. a left lateral or postero-lateral vein. In such a case and depending on the anatomy of the particular subject's heart the most distal electrodes 32, 34, 36 (see FIG. 2) of the quadropolar LV lead 30 can sense and pace the left ventricle and the more proximal electrode(s) 38 can sense and pace the left atrium. Thus, it is possible to determine both interventricular and interatrial delays with a single right atrial lead 40 having at least one electrode 42, a single right ventricular lead 20 with at least one electrode 22, 24 and a multipolar, such as quadropolar, LV lead 30 having some of its electrodes 32, 34, 36 positioned for ventricular pacing and some of the electrodes 38 for atrial pacing.

As mentioned in the foregoing, the system 100 comprises an IMD 300, see FIGS. 2 and 3, which can be in the form of a pacemaker, cardioverter or an intracardiac defibrillator. In an embodiment, the electrode connector 110, the pulse generator 120, 125, the pulse generator controller 130 and the memory 170 of the system 100 are implemented in the IMD 300. The IMD 300 additionally comprises a transceiver 190 configured to conduct wireless communication with a non-implantable data processing unit or device 200 of the system 100. In particular, the transceiver 190 is configured to receive a notification of the candidate interchamber delays. The optional time processor 185 can be arranged in the IMD 300. The width processor 140, the model processor 150 and the delay processor 160 are implemented in the data processing unit 200. The data processing unit 200 additionally comprises or is connected to a transceiver 210 or communication module that is configured to wirelessly communicate with the IMD 300 and in particular transmit notifications of the candidate interchamber delays determined by the delay processor 160 to the IMD for usage therein as CRT settings. The optional EGM processor 180 can be implemented either in the data processing unit in the case of surface ECG measurements, see FIG. 3, or in the IMD 300 in the case of using surface-like ECG measurements based on IEGM signals, see FIG. 2.

In this embodiment, the processing required in order to determine the width parameter values, the parametric model and the candidate interchamber delays is conducted in the data processing unit 200. The data processing unit 200 generally has superior data processing capability as compared to the IMD 300 which is limited in size since it needs to be implanted and is powered by a battery. This embodiment therefore efficiently determines the CRT settings but without draining too much battery power from the IMD 300 since the processing is conducted elsewhere, i.e. in the data processing unit 200.

In an alternative embodiment, the IMD 300 comprises the electrode connector 110, the pulse generator 120, 125, the pulse generator controller 130, the width processor 140, the memory 170, the optional EGM processor 180 and the transceiver 190. The transceiver 190 then transmits width parameter values determined by the width processor 140 to the data processing unit 200 and in turn receives a notification of the candidate interchamber delays. The data processing unit 200 comprises the model processor 150, the delay processor 160 and the transceiver 210 required to communicate with the IMD 300 and receive the width parameter values and transmit the notification of the candidate interchamber delays.

The above disclosed embodiment is particularly suitable when the IMD 300 comprises the EGM processor 180 and the ECG representing signal is obtained from IEGM signals recorded by the IMD 300. In such a case, no communication of this ECG representing signal to the data processing unit 200 is needed since the width processor 140 is already implemented in the IMD 300.

Figure 4:
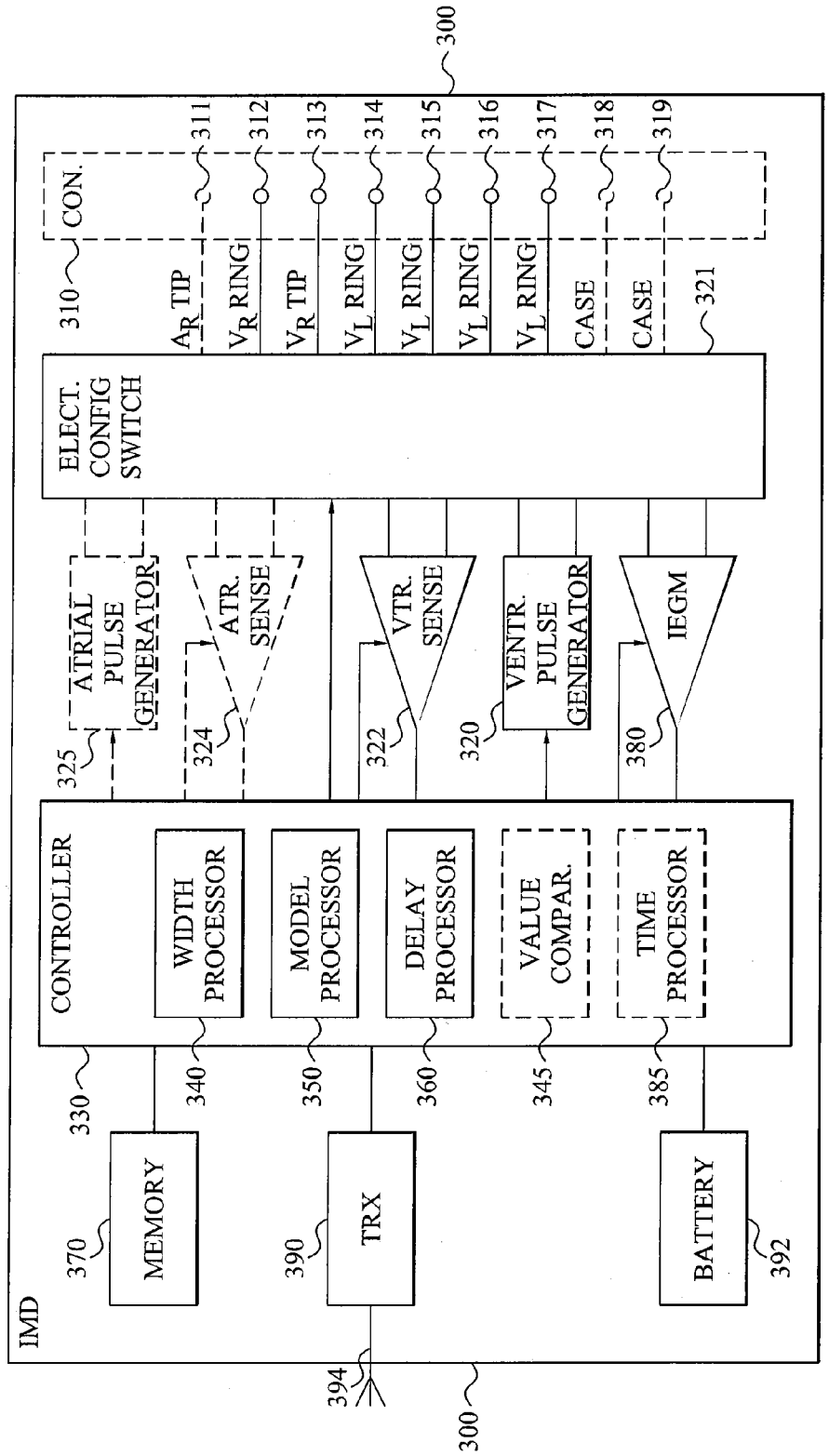
FIG. 4 is a schematic block diagram of an implantable medical device of an embodiment.

A further variant is to have a complete implantable system 100 with all the functions of the system 100 implemented in the IMD 300. This is schematically illustrated in FIG. 4. The figure is a simplified block diagram depicting various components of the IMD 300. While a particular multi-chamber device is shown in the figure, it is to be appreciated and understood that this is done merely for illustrative purposes. Thus, the techniques and methods described below can be implemented in connection with other suitably configured IMDs. Accordingly, the person skilled in the art can readily duplicate, eliminate, or disable the appropriate circuitry in any desired combination to provide an IMD capable of treating the appropriate heart chamber(s) with pacing stimulation and optionally also cardioversion and/or defibrillation.

The IMD 300 comprises a housing, often denoted as can or case in the art. The housing or a portion thereof can act as return electrode for unipolar leads, which is well known in the art. The IMD 300 also comprises the electrode connector 310 having a plurality of terminals 311-319. With reference to FIGS. 2 and 4, the electrode connector 310 is configured to be, during operation in the subject body, electrically connectable to, in this particular example, a left ventricular lead 30, a right ventricular lead 20 and optionally also to a right atrial lead 40. The electrode connector 310 consequently comprises a terminal 311 that is electrically connected to matching electrode terminals of the atrial lead 40 when the atrial lead 40 is introduced in the electrode connector 310.

In an alternative implementation, the IMD 100 is not connectable to a right atrial lead 40 but instead to a left atrial lead configured for implantation in the left atrium. A further possibility is to have an IMD 300 with an electrode connector 310 having sufficient terminals to allow the IMD 300 to be electrically connectable to both a right atrial lead 40 and a left atrial lead. Alternatively, left atrial pacing and sensing can be achieved with at least one of the electrodes 38 of the left ventricular lead 30.

The embodiments, however, do not necessarily have to use any atrial leads unless atrial sensing and pacing are desired. Thus, in such a case, the electrode connector 310 is only connected to a right ventricular lead 20 and a left ventricular lead 30. The terminal 311 of the electrode connector 310 can then be omitted.

In order to support right chamber sensing and pacing, the electrode connector 310 further comprises a right ventricular tip terminal 313 and a right ventricular ring terminal 312, which are adapted for connection to a right ventricular tip electrode 22 and a right ventricular ring electrode 24 of the right ventricular lead 20 implantable in the right ventricle, see FIG. 2.

The electrode connector 310 is also connectable to a left ventricular lead 30. A left ventricular lead 30 is typically implanted in the coronary venous system for safety reasons although implantation inside the left ventricle has been proposed in the art. "Left ventricular lead" 30 is used herein to describe a cardiac lead designed to provide sensing and pacing functions to the left ventricle regardless of its particular implantation site, i.e. inside the left ventricle or in the coronary venous system. The left ventricular lead 30 preferably also comprises multiple electrodes 32-38 that are electrically connectable to corresponding terminals 314-317 of the electrode connector 310.

In the figure, the left ventricular lead 30 is exemplified as multi-electrode or multipolar lead and more correctly a quadropolar lead 30, i.e. having, in total, four electrodes 32-38. The embodiments are, however, not limited to using left ventricular leads of multipolar type, i.e. leads having three or more electrodes. In clear contrast, the left ventricular lead 30 can alternatively be a bipolar lead having a tip electrode and one ring electrode. The number of terminals of the electrode connector 310 should then be reduced to match the number of electrodes of the left ventricular lead 30.

The right ventricular lead 20 could also be a multipolar lead, such as quadropolar lead. The electrode connector 310 would then need to comprise at least three, such as four, terminals to be connected to matching electrode terminals at the proximal end of the multipolar right ventricular lead. Also a combination of multipolar right and ventricular leads are possible and within the scope of the embodiments.

If any of the cardiac leads 20, 30, 40 comprises a shock electrode the electrode connector 310 has a matching terminal configured to be electrically connectable to the shock electrode.

The housing can act as return electrode as mentioned above. In such a case, the electrode connector 310 can have one or more dedicated terminals 318, 319 connected to the housing or the case electrode(s) 50, 52 of the housing illustrated in FIG. 2.

The IMD 300 as illustrated in FIG. 4 comprises an optional atrial pulse generator 325 and a ventricular pulse generator 320 that generate pacing pulses for delivery by the optional atrial lead(s) and the ventricular leads preferably through an electrode configuration switch 321.

It is understood that in order to provide stimulation therapy in different heart chambers, the ventricular and atrial pulse generators 320, 325 may include dedicated, independent pulse generators, multiplexed pulse generators, or shared pulse generators. The pulse generators 320, 325 are controlled by a controller 330 via appropriate control signals, respectively, to trigger or inhibit the stimulating pulses.

The controller 330 is preferably in the form of a programmable microcontroller 330 that controls the operation of the IMD 300. The controller 330 typically includes a microprocessor, or equivalent control circuitry, designed specifically for controlling the delivery of pacing therapy, and may further include RAM or ROM memory, logic and timing circuitry, state machine circuitry, and I/O circuitry. Typically, the controller 330 is configured to process or monitor input signal as controlled by a program code stored in a designated memory block. The type of controller 330 is not critical to the described implementations. In clear contrast, any suitable controller may be used that carries out the functions described herein. The use of microprocessor-based control circuits for performing timing and data analysis functions are well known in the art.

The controller 330 further controls the timing of the stimulating pulses, such as pacing rate, atrioventricular delay, atrial escape interval, etc. as well as to keep track of the timing of refractory periods, blanking periods, noise detection windows, evoked response windows, alert intervals, marker channel timing, etc.

A preferred electronic configuration switch 321 includes a plurality of switches for connecting the desired terminals 311-319 to the appropriate I/O circuits, thereby providing complete electrode programmability. Accordingly, the electronic configuration switch 321, in response to a control signal from the controller 330, determines the polarity of the stimulating pulses (e.g., unipolar, bipolar, combipolar, etc.) by selectively closing the appropriate combination of switches (not shown) as is known in the art.

An optional atrial sensing circuit or detector 324 and a ventricular sensing circuit or detector 322 are also selectively coupled to the optional atrial lead(s) and the ventricular leads through the switch 321 for detecting the presence of cardiac activity in the heart chambers. Accordingly, the ventricular and atrial sensing circuits 322, 324 may include dedicated sense amplifiers, multiplexed amplifiers, or shared amplifiers. The switch 321 determines the "sensing polarity" of the cardiac signal by selectively closing the appropriate switches, as is also known in the art. In this way, the clinician may program the sensing polarity independent of the stimulation polarity. The sensing circuits are optionally capable of obtaining information indicative of tissue capture.

Each sensing circuit 322, 324 preferably employs one or more low power, precision amplifiers with programmable gain and/or automatic gain control, band-pass filtering, and a threshold detection circuit, as known in the art, to selectively sense the cardiac signal of interest.

The outputs of the ventricular and atrial sensing circuits 322, 324 are connected to the controller 330, which, in turn, is able to trigger or inhibit the ventricular and atrial pulse generators 320, 325, respectively, in a demand fashion in response to the absence or presence of cardiac activity in the appropriate chambers of the heart.

Furthermore, the controller 330 is also capable of analyzing information output from the sensing circuits 322, 324 and/or a data acquisition unit or EGM processor 380 to determine or detect whether and to what degree tissue capture has occurred and to program a pulse, or pulse sequence, in response to such determinations. The sensing circuits 322, 324, in turn, receive control signals over signal lines from the controller 330 for purposes of controlling the gain, threshold, polarization charge removal circuitry, and the timing of any blocking circuitry coupled to the inputs of the sensing circuits 322, 324 as is known in the art.

Of the embodiments cardiac signals are applied to inputs of the EGM processor 380 connected to the electrode connector 310. The EGM processor 380 is preferably in the form of an analog-to-digital (ND) data acquisition unit configured to acquire intracardiac electrogram (IEGM) signals, convert the raw analog data into a digital signal that is used directly or further processed in order to generate the ECG representing signal.

The controller 330 of the IMD 300 is coupled to a memory 370 by a suitable data/address bus, wherein the programmable operating parameters used by the controller 330 are stored and modified, as required, in order to customize the operation of the IMD 300 to suit the needs of a particular patient. Such operating parameters define, for example, time threshold, pacing pulse amplitude, pulse duration, electrode polarity, rate, sensitivity, automatic features, and time interval between pacing pulse of an applied pacing pulse sequence.

The memory 370 may also advantageously store width parameter values, maximum and minimum interchamber delays of the defined scheme and candidate interchamber delays determined by the delay processor 360.

Advantageously, the operating parameters of the IMD 300 may be non-invasively programmed into the memory 370 through the transceiver 390 in communication via a communication link with the previously described communication unit of the programmer. The controller 330 activates the transceiver 390 with a control signal. The transceiver 390 can alternatively be implemented as a dedicated receiver and a dedicated transmitter connected to separate antennas or a common antenna, preferably a radio frequency (RF) antenna 394.

The IMD 300 additionally includes a battery 392 that provides operating power to all of the circuits shown in FIG. 4.

In the figure the width processor 340, the model processor 350, the delay processor 360 and the optional value comparator 345 and the optional time processor 385 have been exemplified as being run by the controller 330.

These units can then be implemented as a computer program product stored on the memory 370 and loaded and run on a general purpose or specially adapted computer, processor or microprocessor, represented by the controller 330 in the figure. The software includes computer program code elements or software code portions effectuating the operation of the width processor 340, the model processor 350, the delay processor 360 and the optional value comparator 345 and the optional time processor 385. The program may be stored in whole or part, on or in one or more suitable computer readable media or data storage means that can be provided in an IMD 300.

In an alternative embodiment, the width processor 340, the model processor 350, the delay processor 360 and the optional value comparator 345 and the optional time processor 385 are implemented as hardware units either forming part of the controller 330 or provided elsewhere in the IMD 300.

Figure 6:
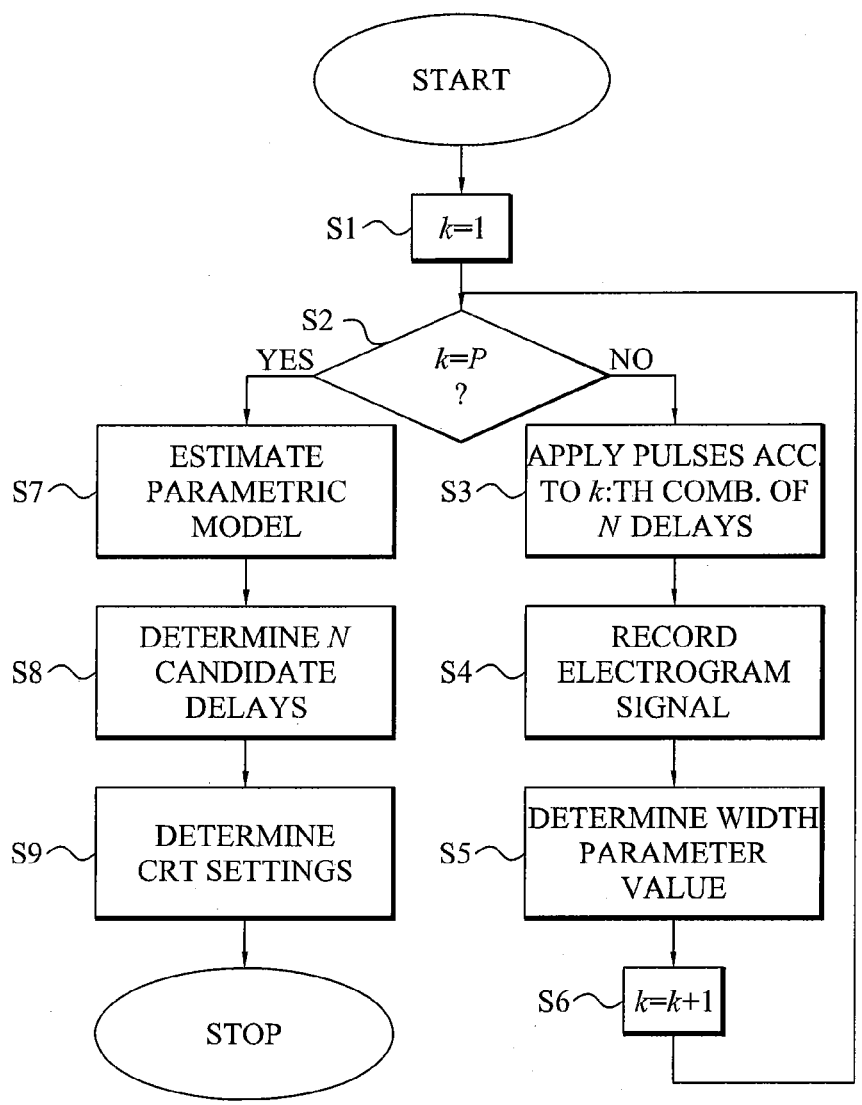
FIG. 6 is a flow diagram illustrating an embodiment for determining cardiac resynchronization therapy settings of an embodiment.

FIG. 6 is a flow diagram illustrating an embodiment of a method of determining CRT settings. The method starts in step S1, where a counter k is set to a start value, such as k=1. A next step S2 investigates whether all combinations of N interchamber delays in the defined scheme have been tested, i.e. whether k=P, where P represents the number of such combinations in the defined scheme. If k≠P the method continues to step S3 where pacing pulses are applied to a first electrode arranged in or in connection with a first heart chamber and to N≥2 electrodes arranged in or in connection with a second heart chamber of the $k^{th}$ combination of interchamber delays of the defined scheme. A next step S4 records an ECG representing signal for the subject from which the width of an R or P wave is determined in step S5 and employed as width parameter value as previously described. The counter k is then increased by one in step S6 and the method returns to step S2. Thus, steps S3 to S5 is repeated once for each combination of N interchamber delays in the defined scheme to thereby obtain the width parameter values. Once all these combinations have been tested and k=P, the method continues from step S2 to step S7. Step S7 estimates an $n^{th}$ order parametric model based on the determined width parameter values from step S5. This parametric model, defining the width parameter as a function of the respective N interchamber delays, is employed in step S8 to determine the N candidate interchamber delays that minimize the width parameter. Finally, CRT settings to use in an IMD are determined based on the N candidate interchamber delays from step S8. The method then ends.

Figure 7:
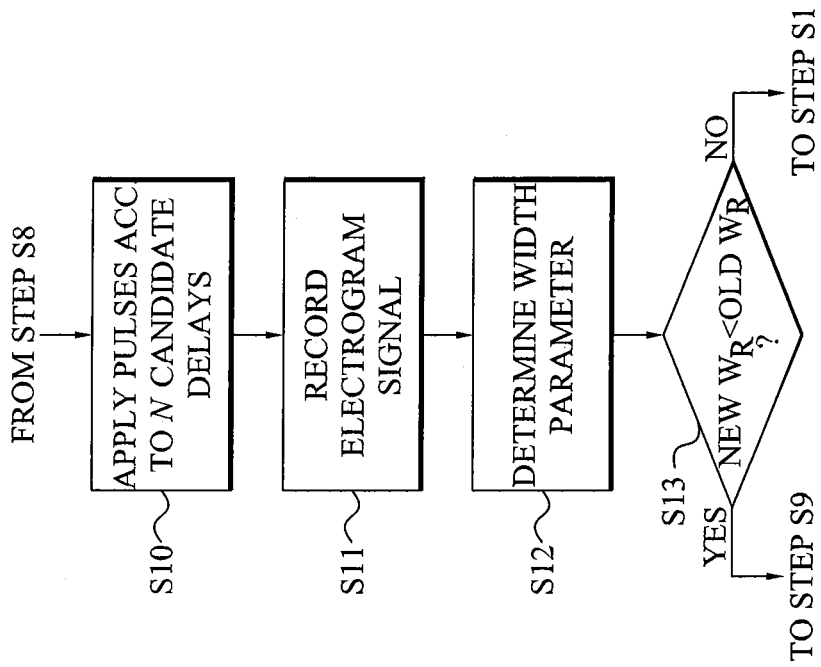
FIG. 7 is a flow diagram illustrating additional, optional steps of the method in FIG. 6.

FIG. 7 is a flow diagram illustrating additional optional steps of the method illustrated in FIG. 6. The method continues from step S8 in FIG. 6. A next step S10 applies pacing pulses to the first electrode and the N electrodes of the N candidate delays determined in step S8 from the parametric model. An ECG signal is then recorded for the subject in step S11 and processed in step S12 in order to determine the candidate width parameter value representing the width of the R or P wave when using the N candidate electrodes as CRT settings. A next step S13 compares this new or candidate width parameter value with the width parameter values determined in step S5 of FIG. 6 when testing the different combination of interchamber delays. If the candidate width parameter value is smaller than all the previously determined width parameter values the method continues to step S9 of FIG. 6, where the N candidate interchamber delays are employed as CRT settings. If the candidate width parameter value, however, is not smaller than all the previous width parameter values in step S13, the method returns to step S1 of FIG. 6 and a new test procedure is initiated in order to generate a new or updated parametric model.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

What is claimed is:

1. A system for determining cardiac resynchronization therapy settings, said system comprising:
    an electrode connector connectable to a first electrode configured to be arranged in connection with a first chamber of a heart of a subject and N≥2 electrodes configured to be arranged in connection with a second chamber of the heart;
    a pulse generator connected to the electrode connector and configured to generate pacing pulses to be applied to the first electrode and the N electrodes;
    a pulse generator controller connected to the pulse generator and configured to control the pulse generator to generate the pacing pulses to be applied to the first electrode and the N electrodes of a defined scheme of interchamber delays defining, for each electrode of the N electrodes, a maximum interchamber delay, a minimum interchamber delay and an intermediate interchamber delay with regard to the timing of applying a pacing pulse to the first electrode;
    a width processor configured to determine, for each combination of N interchamber delays of the defined scheme, a width parameter value representative of a width of a resulting R wave, if the first and second chambers are first and second ventricles, or of a resulting P wave, if the first and second chambers are first and second atria, occurring in an electrocardiogram representing signal recorded for the heart;
    a model processor configured to estimate, based on the width parameter values, an $n^{th}$ order parametric model defining the width parameter as a function of a respective interchamber delay for each electrode of the N electrodes, n≥2;
    a delay processor configured to determine, based on the $n^{th}$ order parametric model and for each electrode of the N electrodes, a candidate interchamber delay that minimizes the width parameter; and
    a memory configured to store cardiac resynchronization settings obtained based on the N candidate interchamber delays.

2. The system of claim 1, wherein the pulse generator controller is configured to control the pulse generator to generate the pacing pulses to be applied to the first electrode and the N electrodes based on the N candidate interchamber delays as the cardiac resynchronization therapy settings.

3. The system of claim 1, wherein n=2 and the model processor is configured to estimate, based on the width parameter values, a quadratic parametric model $$W_R = a + \sum_{i=1}^{N} b_i D_i + \sum_{i=1}^{N} c_i D_i^2 + \sum_{i=1}^{N-1} \sum_{j=i+1}^{N} e_{ij} D_i D_j$$

by estimating the coefficients a, $b_i$, $c_i$, $e_{ij}$ of the quadratic parametric model, wherein $W_R$ represents the width parameter and $D_i$, $D_j$ represents an interchamber delay for electrode i, j of the N electrodes.

4. The system of claim 1, wherein the electrode connector is connectable to two case electrodes provided on a housing of an implantable medical device comprising the electrode connector, the system comprising:
    an electrocardiogram processor configured to generate the electrocardiogram representing signal based on electric signals originating from the heart and sensed by the two case electrodes.

5. The system of claim 1, wherein the pulse generator controller is configured to control the pulse generator to generate the pacing pulses to be applied to the first electrode and the N electrodes of the defined scheme defining, for each electrode of the N electrodes, the maximum interchamber delay, the minimum interchamber delay and the intermediate interchamber delay equal to an average of the maximum interchamber delay and the minimum interchamber delay with regard to the timing of applying the pacing pulse to the first electrode.

6. The system of claim 1, further comprising:
    a transceiver configured to receive a notification of the maximum interchamber delay and the minimum interchamber delay for each electrode of the N electrodes, wherein:
    the memory is configured to store the received notifications of the maximum interchamber delay and the minimum interchamber delay, and
    the pulse generator controller is configured to retrieve the notifications of the maximum interchamber delay and the minimum interchamber delay from the memory.

7. The system of claim 6, further comprising a time processor configured to determine a conduction time corresponding to a time from application of a pacing pulse at the first electrode and up to a time when a depolarization pulse is sensed at an electrode of the N electrodes, wherein
    the pulse generator controller is configured to determine the maximum interchamber delay for the electrode of the N electrodes to be equal to the smallest of the conduction time subtracted by a defined time value and the received notification of the maximum interchamber delay.

8. The system of claim 1, wherein the pulse generator controller is configured to control the pulse generator to generate the pacing pulses of each combination of N interchamber delays of the defined scheme during at least one respiratory cycle.

9. The system of claim 1, further comprising a transceiver configured to transmit a notification of the N candidate interchamber delays to a non-implantable data processing unit and receive an implementation signal from the non-implantable data processing unit, wherein the memory is configured to store the N candidate interchamber delays as the cardiac resynchronization therapy settings based on the implementation signal.

10. The system of claim 1, wherein the width processor is configured to determine a candidate width parameter value occurring in an electrocardiogram representing signal recorded for the heart in response to the pulse generator controller controlling the pulse generator to generate the pacing pulses to be applied to the first electrode and the N electrodes based on the N candidate interchamber delays, the system comprising:

a value comparator configured to compare the candidate width parameter value with width parameter values obtained in response to the pulse generator controller controlling the pulse generator to generate the pacing pulses to be applied to the first electrode and the N electrodes of the defined scheme and generate a grant signal if the candidate width parameter value is smaller than the width parameter values, wherein the memory is configured to store the N candidate interchamber delays as the cardiac resynchronization therapy settings based on the grant signal.

11. The system of claim 1, wherein:

the width processor is configured to determine a candidate width parameter value representative of a width of a resulting wave occurring in an electrocardiogram representing signal recorded for the heart in response to the pulse generator controller controlling the pulse generator to generate the pacing pulses to be applied to the first electrode and the N electrodes based on the N candidate interchamber delays;

the pulse generator controller is configured to control the pulse generator to generate the pacing pulses to be applied to the first electrode and the N electrodes based on a candidate interchamber delay of the N candidate interchamber delays modified with a delta delay;

the width processor is configured to determine an updated width parameter value representative of a width of a resulting R wave, if the first and second chambers are first and second ventricles, or of a resulting P wave, if the first and second chambers are first and second atriums, occurring in an electrocardiogram representing signal recorded for the heart in response to the pulse generator controller controlling the pulse generator to generate the pacing pulses to be applied to the electrode and the N electrodes based on the candidate interchamber delay modified with the delta delay; and the memory is configured to update the cardiac resynchronization therapy settings based on the candidate interchamber delay modified with the delta delay if the updated width parameter value is smaller than the candidate width parameter value.

12. The system of claim 1, wherein:

the electrode connector is connectable to a first ventricular lead comprising a first ventricular electrode and configured to be arranged in a first ventricle of the heart and a second ventricular lead comprising N ventricular electrodes and configured to be arranged in a second ventricle of the heart;

the pulse generator is a ventricular pulse generator configured to generate pacing pulses to be applied to the first ventricular electrode and the N ventricular electrodes;

the pulse generator controller is configured to control the ventricular pulse generator to generate the pacing pulses to be applied to the first ventricular electrode and the N ventricular electrodes of a defined scheme of interventricular delays defining, for each ventricular electrode of the N ventricular electrodes, a maximum interventricular delay, a minimum interventricular delay and an intermediate interventricular delay with regard to the timing of applying a pacing pulse to the first ventricular electrode;

the width processor is configured to determine, for each combination of N interventricular delays of the defined scheme, an R width parameter value representative of a width of a resulting R wave occurring in an electrocardiogram representing signal recorded for the heart;

the model processor is configured to estimate, based on the R width parameter values, the $n^{th}$ order parametric model defining the R width parameter as a function of a respective interventricular delay for each ventricular electrode of the N ventricular electrodes, $n \geq 2$;

the delay processor is configured to determine, based on the $n^{th}$ order parametric model and for each ventricular electrode of the N ventricular electrodes, a candidate interventricular delay that minimizes the R width parameter; and the memory is configured to store cardiac resynchronization settings obtained based on the N candidate interventricular delays.

13. The system of claim 12, wherein the electrode connector is connectable to an atrial electrode configured to be arranged in connection with an atrium of the heart, the system comprising:

an atrial pulse generator connected to the electrode connector and configured to generate pacing pulses to be applied to the atrial electrode, wherein the pulse generator controller is connected to the atrial pulse generator and configured to control the atrial pulse generator to generate pacing pulses to be applied to the atrial electrode and control the ventricular pulse generator to generate the pacing pulses to be applied to the first ventricular electrode and the N ventricular electrodes of the defined scheme after expiry of a defined atrioventricular delay with regard to the timing of applying a pacing pulse to the atrial electrode, the defined atrioventricular delay being smaller than an average intrinsic atrioventricular conduction time of the heart.

14. The system of claim 12, wherein the electrode connector is connectable to a first atrial electrode configured to be arranged in connection with a first atrium of the heart and $M \geq 1$ atrial electrodes configured to be arranged in connection with a second atrium of the heart, the system comprising:

an atrial pulse generator connected to the electrode connector and configured to generate pacing pulses to be applied to the first atrial electrode and the M atrial electrodes, wherein the pulse generator controller is connected to the atrial pulse generator and configured to control the atrial pulse generator to generate the pacing pulses to be applied to the first atrial electrode and the M atrial electrodes of a defined scheme of interatrial delays defining, for each atrial electrode of the M atrial electrodes, a maximum interatrial delay, a minimum interatrial delay and an intermediate interatrial delay with regard to the timing of applying a pacing pulse to the first atrial electrode;

the width processor is configured to determine, for each combination of M interatrial delays of the defined scheme, a P width parameter value representative of a width of a resulting P wave occurring in an electrocardiogram representing signal recorded for the heart;

the model processor is configured to estimate, based on the P width parameter values, an $n^{th}$ order parametric model defining the P width parameter as a function of a respective interatrial delay for each atrial electrode of the M atrial electrodes, $n \geq 2$;

the delay processor is configured to determine, based on the $n^{th}$ order parametric model and for each atrial electrode of the M atrial electrodes, a candidate interatrial delay that minimizes the P width parameter; and the memory is configured to update the cardiac resynchronization therapy settings based on the M candidate interatrial delays.

15. The system of claim 14, wherein the electrode connector is configured to be connected to a right ventricular lead comprising the first ventricular electrode, a right atrial lead comprising the first atrial electrode and a left ventricular lead comprising the N ventricular electrodes and the M atrial electrodes.

16. The system of claim 1, wherein the system comprises:
an implantable medical device comprising the electrode connector, the pulse generator, the pulse generator controller, the memory and a transceiver configured to receive a notification of the candidate interchamber delays; and
a non-implantable data processing unit comprising the width processor, the model processor, the delay processor and a transceiver configured to transmit the notification of the candidate interchamber delays.

17. The system of claim 1, wherein the system comprises:
an implantable medical device comprising the electrode connector, the pulse generator, the pulse generator controller, the width processor, the memory and a transceiver configured to transmit the width parameter values and receive a notification of the candidate interchamber delays; and
a non-implantable data processing unit comprising the model processor, the delay processor and a transceiver configured to receive the width parameter values and transmit the notification of the candidate interchamber delays.

18. The system of claim 1, wherein the system comprises an implantable medical device comprising the electrode connector, the pulse generator, the pulse generator controller, the width processor, the model processor, the delay processor and the memory.

19. A method for determining cardiac resynchronization therapy settings, said method comprising:
applying pacing pulses to a first electrode arranged in connection with a first chamber of a heart of a subject and $N \geq 2$ electrodes arranged in connection with a second chamber of the heart of a defined scheme of interchamber delays defining, for each electrode of the N electrodes, a maximum interchamber delay, a minimum interchamber delay and an intermediate interchamber delay with regard to the timing of applying a pacing pulse to the first electrode;

determining, for each combination of N interchamber delays of the defined scheme, a width parameter value representative of a width of a resulting R wave, if the first and second chambers are first and second ventricles, or of a resulting P wave, if the first and second chambers are first and second atria, occurring in an electrocardiogram representing signal recorded for the heart;

estimating, based on the width parameter values, an $n^{th}$ order parametric model defining the width parameter as a function of a respective interchamber delay for each electrode of the N electrodes, $n \geq 2$;

determining, based on the $n^{th}$ order parametric model and for each electrode of the N electrodes, a candidate interchamber delay that minimizes the width parameter; and determining the cardiac resynchronization settings obtained based on the N candidate interchamber delays.

* * * * *